(12) United States Patent  
Parker

(10) Patent No.: US 7,245,953 B1
(45) Date of Patent: *Jul. 17, 2007

(54) REUSABLE PULSE OXIMETER PROBE AND DISPOSABLE BANDAGE APPARATII

(75) Inventor: Brent Parker, Murrieta, CA (US)

(73) Assignee: Masimo Corporation, Irvine, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 10/287,795

(22) Filed: Nov. 5, 2002

Related U.S. Application Data

(63) Continuation-in-part of application No. 09/758,038, filed on Jan. 11, 2001, now Pat. No. 6,684,091, which is a continuation-in-part of application No. 09/417,898, filed on Oct. 14, 1999, now Pat. No. 6,343,224, which is a continuation-in-part of application No. 09/289,647, filed on Apr. 12, 1999, now Pat. No. 6,144,868.

(60) Provisional application No. 60/331,130, filed on Nov. 9, 2001.

(51) Int. Cl.
*A61B 5/00* (2006.01)

(52) U.S. Cl. ...................... 600/344; 600/310

(58) Field of Classification Search ............... 600/310, 600/322, 323, 340, 344, 473, 476
See application file for complete search history.

(56) References Cited

U.S. PATENT DOCUMENTS 3,463,142 A    8/1969    Harte et al.
3,647,299 A    3/1972    Lavallee
3,740,570 A    6/1973    Kaelin et al.
3,799,672 A    3/1974    Vurek
4,086,915 A    5/1978    Kofsky et al.
4,169,976 A   10/1979    Cirri
4,182,977 A    1/1980    Stricklin, Jr.
4,308,456 A   12/1981    van der Gaag et al.
4,346,590 A    8/1982    Brown
4,407,290 A   10/1983    Wilber
4,449,821 A    5/1984    Lee
4,480,886 A   11/1984    Bergamin
4,580,867 A    4/1986    Wright et al.
4,621,643 A   11/1986    New, Jr. et al.
4,653,498 A    3/1987    New, Jr. et al.
4,685,464 A    8/1987    Goldberger et al.
4,700,708 A   10/1987    New, Jr. et al.
4,770,179 A    9/1988    New, Jr. et al.
4,830,014 A    5/1989    Goodman et al.
4,848,901 A    7/1989    Hood, Jr.
4,865,038 A    9/1989    Rich et al.
4,877,322 A   10/1989    Hill
4,913,150 A    4/1990    Cheung et al.
4,942,877 A    7/1990    Sakai et al.

(Continued)

FOREIGN PATENT DOCUMENTS

AU        745306        5/2000

(Continued)

*Primary Examiner*—Eric F. Winakur
(74) *Attorney, Agent, or Firm*—Knobbe Martens Olson & Bear LLP

(57) ABSTRACT

Disposable bandage apparatus for use in oximetry having adhesive on at least a portion of at least one face thereof, at least one plastic receptacle mounted thereon and a radiation transparent window bounded by said receptacle.

22 Claims, 3 Drawing Sheets

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,058,588 A | 10/1991 | Kaestle |
| 5,069,213 A | 12/1991 | Polczynski |
| 5,090,410 A | 2/1992 | Saper et al. |
| 5,094,240 A | 3/1992 | Muz |
| 5,113,862 A | 5/1992 | Mortazavi |
| 5,140,228 A | 8/1992 | Biegel |
| 5,158,323 A | 10/1992 | Yamamoto et al. |
| 5,163,438 A | 11/1992 | Gordon et al. |
| 5,170,786 A | 12/1992 | Thomas et al. |
| 5,209,230 A | 5/1993 | Swedlow et al. |
| 5,246,003 A | 9/1993 | DeLonzor |
| 5,249,576 A | 10/1993 | Goldberger et al. |
| 5,267,562 A | 12/1993 | Ukawa et al. |
| 5,287,853 A | 2/1994 | Vester et al. |
| 5,308,919 A | 5/1994 | Minnich |
| 5,337,744 A | 8/1994 | Branigan |
| 5,387,122 A | 2/1995 | Goldberger et al. |
| 5,397,247 A | 3/1995 | Aoki et al. |
| 5,431,170 A | 7/1995 | Mathews |
| 5,437,275 A | 8/1995 | Amundsen et al. |
| 5,452,717 A | 9/1995 | Branigan et al. |
| 5,482,036 A | 1/1996 | Diab et al. |
| 5,490,505 A | 2/1996 | Diab et al. |
| 5,494,043 A | 2/1996 | O'Sullivan et al. |
| 5,507,286 A | 4/1996 | Solenberger |
| 5,515,169 A | 5/1996 | Cargill et al. |
| 5,533,511 A | 7/1996 | Kaspari et al. |
| 5,590,649 A | 1/1997 | Caro et al. |
| 5,619,992 A | 4/1997 | Guthrie et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,660,567 A | 8/1997 | Nierlich et al. |
| 5,664,270 A | 9/1997 | Bell et al. |
| 5,673,693 A | 10/1997 | Solenberger |
| 5,678,544 A | 10/1997 | DeLonzor et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,786,592 A | 7/1998 | Hök |
| 5,791,347 A | 8/1998 | Flaherty et al. |
| 5,810,734 A | 9/1998 | Caro et al. |
| 5,817,008 A | 10/1998 | Rafert et al. |
| 5,817,010 A | 10/1998 | Hibl |
| 5,823,950 A | 10/1998 | Diab et al. |
| 5,830,131 A | 11/1998 | Caro et al. |
| 5,833,618 A | 11/1998 | Caro et al. |
| RE36,000 E | 12/1998 | Swedlow et al. |
| 5,860,919 A | 1/1999 | Kiani-Azarbayjany et al. |
| 5,879,373 A | 3/1999 | Roper et al. |
| 5,890,929 A | 4/1999 | Mills et al. |
| 5,904,654 A | 5/1999 | Wohltmann et al. |
| 5,910,108 A | 6/1999 | Solenberger |
| 5,919,133 A | 7/1999 | Taylor et al. |
| 5,919,134 A | 7/1999 | Diab |
| 5,934,925 A | 8/1999 | Tobler et al. |
| 5,940,182 A | 8/1999 | Lepper, Jr. et al. |
| 5,991,648 A | 11/1999 | Levin |
| 5,995,855 A | 11/1999 | Kiani et al. |
| 5,997,343 A | 12/1999 | Mills et al. |
| 5,999,834 A | 12/1999 | Wang et al. |
| 6,002,952 A | 12/1999 | Diab et al. |
| 6,011,986 A | 1/2000 | Diab et al. |
| 6,014,576 A | 1/2000 | Raley |
| 6,027,452 A | 2/2000 | Flaherty et al. |
| 6,036,642 A | 3/2000 | Diab et al. |
| 6,045,509 A | 4/2000 | Caro et al. |
| 6,061,584 A | 5/2000 | Lovejoy et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,308,089 B1 | 10/2001 | von der Ruhr et al. |
| 6,321,000 B1 | 11/2001 | King |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kian et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,381,489 B1 | 4/2002 | Ashibe |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,519,487 B1 * | 2/2003 | Parker ........................ 600/344 |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 * | 1/2004 | Parker ........................ 600/344 |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,585 B1 * | 4/2004 | Parker ........................ 600/344 |
| 6,725,075 B2 | 4/2004 | Al-Ali |
| 6,735,459 B2 * | 5/2004 | Parker ........................ 600/344 |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |

| | | |
|---|---|---|
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 2004/0147824 A1 | 7/2004 | Diab et al. |
| 2005/0245797 A1 | 11/2005 | Al-Ali et al. |

FOREIGN PATENT DOCUMENTS

| | | |
|---|---|---|
| CA | 2 346 639 | 4/2000 |
| CA | 2 366 493 | 11/2002 |
| EP | 019 478 | 11/1980 |
| EP | 0 745 348 | 12/1996 |
| EP | 1 222 894 | 7/2002 |
| JP | 5275746 | 10/1993 |
| WO | WO 88/10462 | 12/1998 |
| WO | WO 99/53831 | 10/1999 |
| WO | WO 00/21433 | 4/2000 |
| WO | WO 00/42911 | 7/2000 |
| WO | WO 01/03574 | 1/2001 |

* cited by examiner

REUSABLE PULSE OXIMETER PROBE AND DISPOSABLE BANDAGE APPARATII

REFERENCE TO RELATED APPLICATION

This application is the subject of provisional application Ser. No. 60/331,130 filed Nov. 9, 2001 and entitled REUSABLE PULSE OXIMETER PROBE AND DISPOSABLE BANDAGE APPARATUS which is incorporated herein by reference. This application is a continuation-in-part application of Ser. No. 09/758,038 filed Jan. 11, 2001 now U.S. Pat. No. 6,684,091 entitled REUSABLE PULSE OXIMETER PROBE AND DISPOSABLE BANDAGE METHOD, which in turn is a continuation-in-part of application Ser. No. 09/417,898 filed Oct. 14, 1999 now U.S. Pat. No. 6,343,224, which in turn is a continuation-in-part of Ser. No. 09/289,647 filed Apr. 12, 1999 (now U.S. Pat. No. 6,144,868).

BACKGROUND OF THE INVENTION

Heretofore the use of pulse oximeter probes has been limited to the use of a costly, reusable probe, which is contaminated by use on a patient, or cheaper, single-use, disposable probes, which in the aggregate, amount to a considerable cost for a healthcare institution. The current applicant in his U.S. Pat. Nos. 6,144,868, 6,321,100 and 6,343,224, and subsequent continuations-in-part, has described a reusable pulse oximeter probe with modular probe housings and a disposable bandage apparatus having at least two modular receptacles thereon. The probe housings can matedly engage said bandage receptacles, and transmit and receive signals through the blood-profused flesh of a patient when said probe and bandage apparatus are resident on a patient. After use on a subject, the disposable bandage apparatus is discarded and the reusable probe can then be reused on another patient in conjunction with a new disposable bandage apparatus.

Although the previously described bandage is very good, there are, in some instances, cases whereby it would be advantageous to offer disposable bandage apparatii having different designs in order for them to work efficiently in a particular situation.

In some cases, female patients will have long fingernails. When a bandage apparatus includes two receptacles with a particular, fixed spacing between the receptacles, it can be difficult, if not impossible, to align the receptacles exactly opposite one another on the finger in order to allow for proper transmission and reception of signals between the light-emitting diode and the photocell detector. In these cases, it could be preferable to offer two bandage apparatii that may be placed independently of one another.

In many cases, it could also be advantageous to have two bandage apparatii connected by a biasing member in order to assure exact alignment of the light-emitting diode and photocell detector on either side of a patient's digit.

Where patients have low peripheral profusion, it may be necessary to affix a probe to an ear or a forehead. Several designs of bandage apparatii are therefore disclosed for these applications.

In addition, when pulse oximetry is used on the forehead, it would be necessary to use a reflectance sensor and corresponding bandage apparatus. Disclosure is therefore made for this type of device as well.

The Present Invention

The following disclosure offers various improvements on a disposable bandage apparatus and a reusable pulse oximeter probe.

What is presently disclosed is at least one bandage apparatus having adhesive on at least a portion of at least one face thereof, and at least one plastic female receptacle mounted thereon; and at least one other bandage apparatus having adhesive on at least a portion of at least one face thereof, and having at least one plastic female receptacle mounted thereon, wherein said apparatii may be placed on a patient and wherein said at least one female receptacle of each at least one bandage apparatus can matedly and removably engage at least one housing of a reusable pulse oximeter probe, said at least one housing incorporating thereon or therein at least one photocell detector, or at least one light-emitting diode.

In addition, the apparatii, as disclosed above, may be connected by a biasing member.

Further, a reusable reflectance probe is disclosed said probe having at least one modular plastic housing said at least one housing having incorporated therein or thereon at least one light-emitting diode, and at least one photocell detector, wherein said probe housing can matedly and removably engage the plastic female receptacle of a disposable bandage apparatus, in order to aid in sending and receiving oximetry signals through the blood-profused flesh of a patient.

Further disclosed is a bandage apparatus for use in reflectance oximetry, said bandage apparatus comprising at least one bandage strip having adhesive on at least a port of at least one face thereof, and having at least one female receptacle mounted thereon, said female receptacle having the capacity to matedly and removably engage the housing of a reusable pulse oximeter probe.

In addition, disclosure is made for a bandage apparatus system for use in reflectance oximetry, said bandage apparatus system comprising at least one bandage strip having adhesive on at least a portion of at least one face thereof, and having at least one plastic female receptacle mounted thereon, said female receptacle having the capacity to matedly and removably engage the housings of different probes, said probes having been designed to replace a multiplicity of manufacturer's reusable pulse oximeter probes, wherein said probe housings are designed to removably and matedly engage said bandage apparatus.

DESCRIPTION OF THE DRAWINGS

The above and other advantages of the invention will become clear when considered with the following specification and accompanying drawings wherein.

DETAILED DESCRIPTION OF THE INVENTION

The Independent Bandage Apparatii

Figure 1:
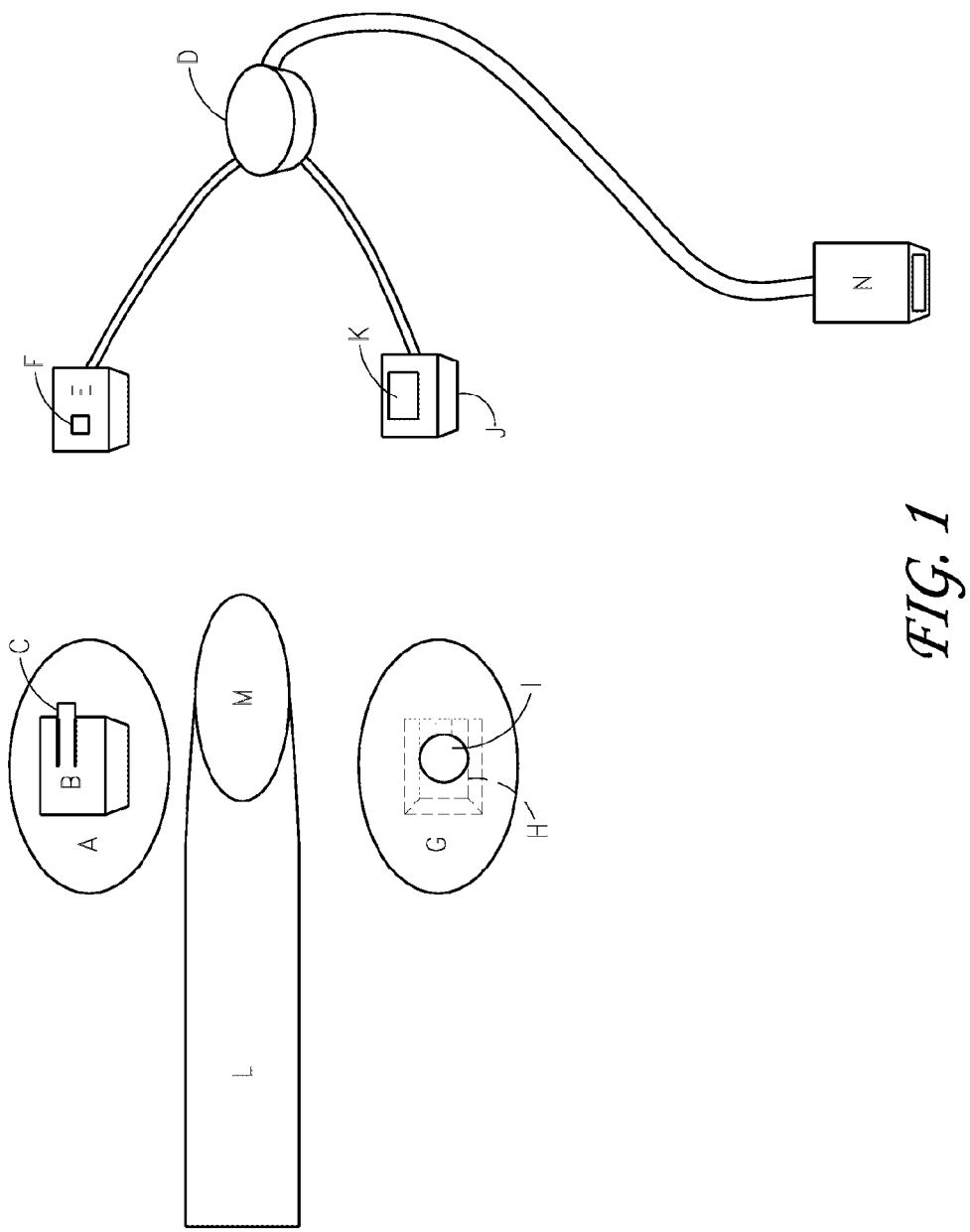
FIG. 1 is an illustration of individual bandage apparatii for more precise placement of a human digit.

The independent bandage apparatii are comprised of a discrete bandage strip, FIG. 1, Item A, which has mounted thereon, a plastic female receptacle, FIG. 1, Item B, said female receptacle having a locking lever FIG. 1, Item C. The female receptacle, FIG. 1, Item B is designed to matedly engage at least one reusable probe housing, FIG. 1, Item E, and to removably retain the probe housing within the female bandage receptacle by means of a protrusion on the locking lever which can removably lodge in an indentation, FIG. 1, Item E, in the probe housing. FIG. 1, Item A, represents a view of the superior side of the bandage apparatus and FIG. 1, Item E is a view of the superior side of the reusable probe housing.

A human finger is represented by FIG. 1, Item L, and a fingernail is shown as FIG. 1, Item M.

Figure 2:
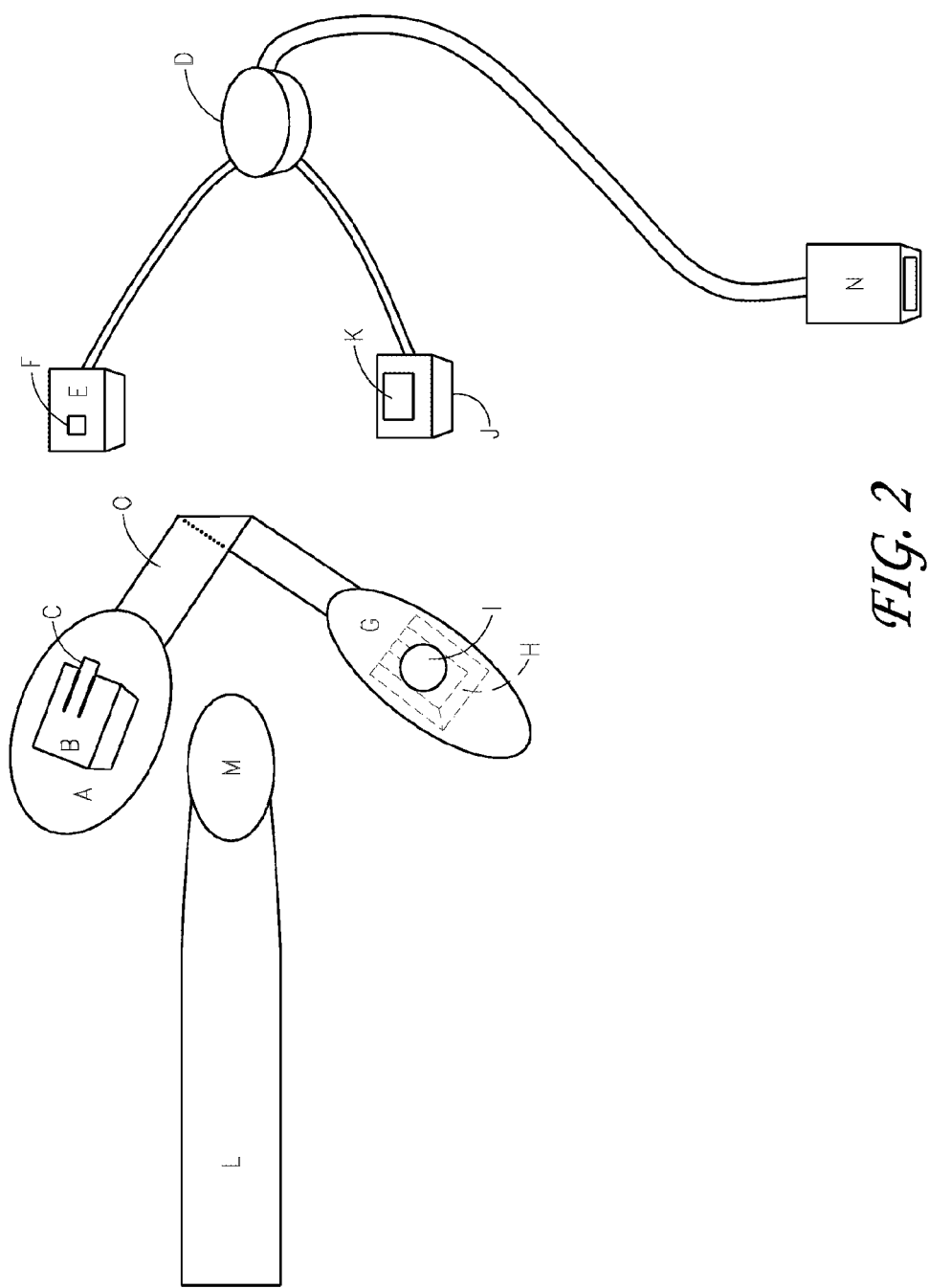
FIG. 2 illustrates individual bandage apparatii connected by a biasing member.

The reusable probe, FIG. 2, Item D, which incorporates housings, FIG. 2, Items E and J, and a connector FIG. 2, Item N, for connecting the probe to the oximeter is not a part of this invention and is shown for illustration purposes only.

The second bandage apparatus is shown in its inferior view as FIG. 2, Item G, and, in this illustration, would be adhered to the underside of the finger. This inferior view illustrates a radiation transparent window, FIG. 2, Item I, which is typical of both bandage apparatii, said radiation transparent windows being designed to align with the radiation transparent windows, FIG. 2, Item K, of the probe housings. FIG. 2, Item J represents an inferior view of the probe housing and illustrates the radiation transparent window that is typical of both probe housings. FIG. 2, Item O represents the biasing member that is designed to incline the two apparatii towards each other, thus giving exact alignment of the radiation transparent windows on either side of the human digit.

Figure 3:
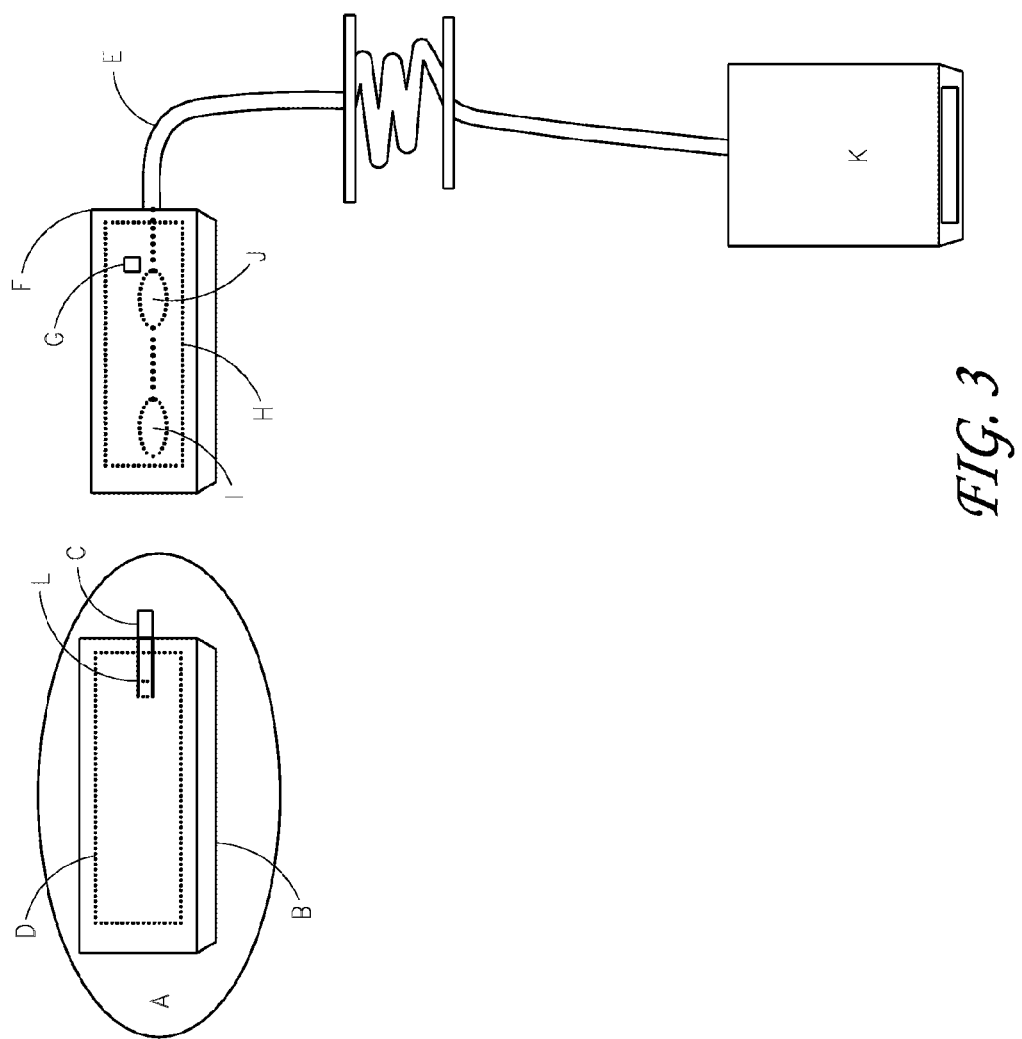
FIG. 3 illustrates a reusable reflectance probe wherein the light-emitting diode and photocell detector of the probe are incorporated into a single probe housing, and it also illustrates a bandage apparatus incorporating one female receptacle for matedly and removably engaging a reflectance probe housing having at least one light-emitting diode and at least one photocell detector.

Description of the Reflectance Probe Having the Light Emitting Diode and Photocell Detector Incorporated into a Plastic Housing and the Bandage Apparatus Designed to Matedly Engage said Probe Housing The reflectance probe having a light emitting diode and photocell detector incorporated into a single plastic housing is shown as FIG. 3, Item F. The probe includes at least one light emitting diode, FIG. 3, Item I, and at least one photocell detector, FIG. 3, Item J, wherein said optical components are incorporated into a plastic housing, FIG. 3, Item F. The housing F also incorporates at least on radiation transparent window, FIG. 3, Item H, which allows for the transmission and/or reception of infrared light through the blood-profused flesh of a patient.

The housing F is designed to matedly and removably engage a female bandage receptacle, FIG. 3, Item B, and incorporates a recessed notch, FIG. 3, Item G, for the reception of a protrusion, FIG. 3, Item L, on the locking lever of the female bandage receptacle, FIG. 3, Item C, thus removably retaining the probe housing within the female bandage receptacle. The bandage apparatus also includes at least one radiation transparent window, FIG. 3, Item A, which is in alignment with the radiation transparent window of the probe housing, FIG. 3, Item H, when said probe housing is resident in said bandage receptacle.

The female bandage receptacle also utilizes at least one bandage strip, FIG. 3, Item A, for adhering the bandage apparatus to a patient.

The reflectance probe also incorporates a connector, FIG. 3, Item K, for electrically connecting the probe to an oximeter, said oximeter not being a part of this invention.

Method of Use for the Independent Bandage Apparatii

For use on each individual patient, the independent bandage apparatii are utilized in the following manner:

Firstly, the adhesive backing is removed on one of the apparatii and the apparatus is adhered to the fingernail of a patient. The adhesive backing on the second apparatus is then removed and the apparatus is adhered to the inferior side of the finger in exact alignment with the first apparatus. Once the bandage apparatii are in place, the probe housings can then be inserted into the female bandage receptacles in order to monitor the patient.

When there is reason to remove the probe, this is accomplished by lifting up on the locking levers thus releasing the probe housings from the bandage receptacles.

When monitoring is complete, the probe can be removed from the bandage apparatii and can be reused on another patient in conjunction with new bandage apparatii.

Method of Use for the Bandage Apparatii Linked by a Biasing Member

For use on each individual patient, the bandage apparatii incorporating a biasing member is utilized as follows:

Firstly, the adhesive backing is removed on each individual apparatus. Each apparatus is then adhered to the superior and inferior sides of the finger, respectively, with the biasing member protruding off of the distal portion of the finger.

Once the bandage apparatii are in place, the probe housings can then be inserted into the female bandage receptacles in order to monitor the patient.

When there is reason to remove the probe, this is accomplished by lifting up on the locking levers thus releasing the probe housings from the female bandage receptacles.

When monitoring is complete, the probe can be removed from the bandage apparatii and can be reused on another patient in conjunction with a new bandage apparatus with linked apparatii.

Method of Use for the Reflectance Probe having the Light Emitting Diode and Photocell Detector Incorporated into a Plastic Housing and the Bandage Apparatus Designed to Matedly Engage said Probe Housing For use on each individual patient, the reflectance probe and bandage apparatus is used as follows:

Firstly, the adhesive backing is removed from the adhesive strip of the bandage apparatus and it is adhered to the patient. The probe housing is then inserted into the bandage apparatus and the patient can be monitored.

When there is reason to remove the probe, this is accomplished by lifting up on the locking lever thus releasing the probe housing from the female bandage receptacle.

When monitoring is complete, the probe can be removed from the female bandage apparatus and can be reused on another patient in conjunction with new bandage apparatus.

Advantages of the Present Inventions

Independent bandage apparatii can offer more flexibility to the caregiver for placement on patients with long fingernails or when pulse oximetry is used on the ear or forehead Independent bandage apparatii linked by a biasing member can assure proper alignment between the receptacles of the apparatii and thus the light emitting diode and photocell detector of the probe For reflectance pulse oximetry, it would be an advantage to have a single probe housing incorporating both the photocell detector and light emitting diode of the probe and for removably and matedly attaching said probe housing with a single female bandage receptacle.

While the invention has been described in relation to preferred embodiments of the invention, it will be appreciated that other embodiments, adaptations and modifications of the invention will be apparent to those skilled in the art.

What is claimed is:

1. An oximetry apparatus comprising:
a first discrete bandage strip apparatus having adhesive on at least a portion of at least one face thereof, and at least one receptacle mounted thereon; and
a second discrete bandage strip apparatus having adhesive on at least a portion of at least one face thereof, and having at least one receptacle mounted thereon;
wherein said first and second discrete bandage strip apparatii may be positioned on a patient, wherein said at least one receptacle of said first discrete bandage strip apparatus can matedly and removably engage a first housing of a reusable pulse oximeter probe, said first housing incorporating thereon or therein at least one photocell detector, wherein said at least one receptacle of said second discrete bandage strip apparatus can matedly and removably engage a second housing of a reusable pulse oximeter probe, said second housing incorporating thereon or therein at least one light emitting diode, and wherein said first discrete bandage strip apparatus is coupled to said second discrete bandage strip apparatus.

2. The oximetry bandage apparatus of claim 1, wherein said first discrete bandage strip apparatus is coupled to said second discrete bandage strip apparatus by a biasing member.

3. An optical probe system capable of sensing a physiological parameter, the system comprising:
a first bandage comprising a first receptacle, the first receptacle being configured to be removably coupled to a probe emitter;
a second bandage comprising a second receptacle, the second receptacle being configured to be removably coupled to a probe detector; and
a biasing member coupled between the first bandage and the second bandage;
wherein the first and second bandages are configured to be positioned generally opposite each other on an appendage of a patient for sensing a physiological parameter of the patient.

4. The optical probe system of claim 3, additionally comprising a probe emitter and a probe detector configured to be removably coupled to said first and second bandage receptacles in an oximetry system.

5. The optical probe system of claim 3, wherein the appendage of the patient is a finger.

6. The optical probe system of claim 3, wherein the first and second bandages are adapted for single use application in an oximetry system.

7. The optical probe system of claim 3, wherein the first and second receptacles each comprise an aperture.

8. The optical probe system of claim 3, wherein the first and second receptacles each comprise a radiation transparent window.

9. The optical probe system of claim 3, wherein the first and second receptacles each substantially enclose the probe emitter and the probe detector, respectively, when engaged.

10. A disposable portion of an optical probe usable to determine at least one physiological parameter, the disposable portion comprising:
a first bandage portion including adhesive on at least a portion of at least one face thereof and comprising a first receptacle configured to be removably coupled to a probe emitter; and
a second bandage portion including adhesive on at least a portion of at least one face thereof and comprising a second receptacle configured to be removably coupled to a probe detector, the first and second adhesive bandage portions configured to cooperate to position said probe emitter generally opposite said probe detector when said disposable portion is removably attached to a patient and said probe emitter and probe detector are respectively coupled to said first and second receptacles, wherein the first bandage portion is coupled with the second bandage portion via a biasing member.

11. The apparatus of claim 10, wherein said first and second bandage portions are adapted for single use application in an oximetry system.

12. The apparatus of claim 10, wherein the first bandage portion and the second bandage portion each comprise a radiation transparent window.

13. The apparatus of claim 10, wherein the bandage apparatus comprises an adhesive backing.

14. The apparatus of claim 10, wherein the first bandage portion and the second bandage portion are discrete bandages.

15. The apparatus of claim 10, wherein the first and second receptacles each comprise an aperture.

16. The apparatus of claim 10, wherein the first and second receptacles each comprise a radiation transparent window.

17. The apparatus of claim 10, wherein the first and second receptacles each substantially enclose the probe emitter and the probe detector, respectively, when engaged.

18. The apparatus of claim 10, wherein the first and second receptacles each comprise a locking mechanism for matedly and removably engaging said probe emitter and probe detector, respectively.

19. A bandage sensor system comprising:
a bandage apparatus including adhesive on at least a portion of at least one face thereof, said bandage apparatus including first and second receptacles mounted thereon, wherein said first and second receptacles are capable of removably mating with reusable sensor elements, wherein said bandage apparatus comprises a first discrete bandage strip and a second discrete bandage strip and the first discrete bandage strip is coupled with said second discrete bandage strip by a biasing member.

20. The bandage sensor system of claim 19, additionally comprising a first reusable sensor element and a second reusable sensor element.

21. The bandage sensor system of claim 20, wherein the first reusable sensor element includes a probe emitter.

22. The bandage sensor system of claim 20, wherein the second reusable sensor element includes a probe detector.

* * * * *